United States Patent
Leising et al.

(10) Patent No.: US 9,950,988 B2
(45) Date of Patent: Apr. 24, 2018

(54) METHOD FOR THE SYNTHESIS OF ALPHA/ALPHA-PRIME-ALCOXYLATED GLYCEROL LINEAR CARBONIC ESTERS

(71) Applicants: CHRYSO, Issy les Moulineaux (FR); Institut National Polytechnique de Toulouse, Toulouse (FR); INSTITUT NATIONAL DE LA RECHERCHE AGRONOMIQUE (INRA), Paris (FR)

(72) Inventors: Frédéric Leising, Avilly Saint Leonard (FR); Zéphirin Mouloungui, Toulouse (FR)

(73) Assignees: CHRYSO, Issy les Moulineaux (FR); INSTITUT NATIONAL POLYTECHNIQUE DE TOULOUSE, Toulouse (FR); INSTITUT NATIONAL DE LA RECHERCHE AGRONOMIQUE (INRA), Paris (FR)

( * ) Notice: Subject to any disclaimer, the term of this patent is extended or adjusted under 35 U.S.C. 154(b) by 182 days.

(21) Appl. No.: 14/655,690

(22) PCT Filed: Dec. 20, 2013

(86) PCT No.: PCT/FR2013/053225
§ 371 (c)(1),
(2) Date: Jun. 25, 2015

(87) PCT Pub. No.: WO2014/102495
PCT Pub. Date: Jul. 3, 2014

(65) Prior Publication Data
US 2015/0329468 A1 Nov. 19, 2015

(30) Foreign Application Priority Data
Dec. 26, 2012 (FR) .................... 12 62796

(51) Int. Cl.
*C07C 69/96* (2006.01)
*C07C 68/06* (2006.01)

(52) U.S. Cl.
CPC ............ *C07C 69/96* (2013.01); *C07C 68/06* (2013.01)

(58) Field of Classification Search
None
See application file for complete search history.

(56) References Cited

U.S. PATENT DOCUMENTS

2004/0198991 A1   10/2004   Stone

FOREIGN PATENT DOCUMENTS

| EP | 2151465 A1 | 2/2010 |
| FR | 2733232 A1 | 10/1996 |
| FR | 2778182 A1 | 11/1999 |
| FR | 2874217 A1 | 2/2006 |
| WO | 2008074450 A2 | 6/2008 |

OTHER PUBLICATIONS

Hu Y et al., 3-Deoxy-3-substituted-d-myo-inositol imidazolyl ether lipid phosphates and carbonate as inhibitors of the phosphatidylinositol 3-kinase pathway and cancer cell growth, Bioorganic & Medicinal Chemistry Letters, Pergamon, vol . 11, No. 2, Jan. 1, 2001 (Jan. 1, 2001), pp. 173-176, XP004314841, ISSN: 0960-894X, DOI: 10.1016/S0960-894X(00)00640-5 cited in the application compound 6.

Ezhova N N et al., Glycerol carboxylation to glycerol carbonate in the presence of rhodium complexes with nitrogen-containing macroligands, Petroleum Chemistry, Nauka/Interperiodica, MO, vol. 52, No. 6, Nov. 6, 2012 (Nov. 6, 2012), pp. 416-421, XP035134264, ISSN: 1555-6239, DOI: 10.1134/S0965544112060060 cited in the application reaction 2; p. 418; table 2.

Database Beilstein Beilstein Institute for Organic Chemistry, Frankfurt-Main, DE; 1994, RX-ID: 4173540, XP002714150, cited in the application the whole document Nedolya, et al., "Vinyl Ethers Containing a Cyclocarbonate Group." Russian Journal of Organic Chemistry, vol. 30, No. 4, 1994, pp. 599-603.

G. Rokicki, "Alphatic cyclic carbonates and spiroorthocarbonates as monomers." Prog. Polym. Sci. 25 (2000) pp. 259-342.

He, et al., "Synthesis, characterization and ring-opening polymerization of a novel six-membered cyclic carbonate bearing pendent allyl ether group." Polymer 49 (2008) pp. 1185-1190.

*Primary Examiner* — Michael Barker
(74) *Attorney, Agent, or Firm* — Knobbe, Martens, Olson & Bear, LLP

(57) ABSTRACT

A method for the synthesis of α/α'-alcoxylated glycerol linear carbonic esters, wherein the following are brought into contact at a reaction temperature lower than 220° C.: a quantity of at least one precursor selected from the group consisting of α/α'-alcoxylated glycerol cyclo-carbonates; a quantity of at least one catalyst selected from the group consisting of metal oxides, Lewis acids, organometallic catalysts and mineral bases; and a quantity of at least one organic primer. A composition containing at least one novel α/α'-alkoxylated glycerol linear carbonic ester.

5 Claims, No Drawings

METHOD FOR THE SYNTHESIS OF ALPHA/ALPHA-PRIME-ALCOXYLATED GLYCEROL LINEAR CARBONIC ESTERS

FIELD OF THE INVENTION

The invention concerns a method for synthesizing novel compounds called α/α'-alkoxylated (alpha/alpha-prime alkoxylated) glycerol linear carbonic esters, in particular in the form of oligomers of α/α'-alkoxylated glycerol linear carbonic esters. The invention also relates to the novel compounds thus obtained, to a composition comprising at least one such novel α/α'-alkoxylated glycerol linear carbonic ester and to the uses of these novel compounds.

DESCRIPTION OF THE RELATED ART

It is known that non-alkoxylated high molecular weight polymers can be produced from 6-membered cyclic carbonates in the presence of anionic initiators such as metal alkoxides ($Li^+$, K, alkaline carbonate, metal alkyl, metal alcoholate).

A cationic polymerisation method is known of a 6-membered cyclic carbonate carrying a pendent allyl group linked to the carbonate ring via an ether bridge. To contain a pendent ether bridge, the monomer must first be O-etherified to maintain the O-allyl ether group in the resulting polycarbonate. The publication <<Synthesis, characterization and ring-opening polymerization of a novel six-membered cyclic carbonate bearing pendent allyl ether group>> He F. et al., (2008), Polymer, 49, 1185-1190, describes a method for polymerizing a 6-membered cyclic carbonate monomer of glycerol carrying an allyl ether, which leads to β-alkyloxylated glycerol carbonate polymers. This method does not allow the obtaining of α/α'-alkoxylated linear glycerol carbonates. In particular, while the opening of 6-membered ring is relatively easy, this is not the case for a 5-membered ring.

The following are known:
- from EP 2 151 465: a catalytic method for polymerising trimethylene carbonate derived from renewable resources;
- from Nedlova N A et al. (1994), Russian Journal of Organic Chemistry, 30, 599-603 and Ezhova et al., (2012), Petroleum Chemistry, 50(20), 416-421: methods for synthesizing urethane compounds;
- from WO 2008/074450: non-peptide nitrated renin-inhibiting compounds;
- from Hu Y et al., (2001), Bioorganic Medicinal Chemistry Letters, 11, 173-176 and from US 2004/0198991: alkoxylated linear glycerol carbonates.

The general study <<Aliphatic cyclic carbonates and spiroorthocarbonates as monomers>>, Rokicki G., (2000), Prog. Polym. Sci., 25, pp 259-342 reports on the polymerisation of ethylene carbonate and propylene carbonate in the presence of a transesterification catalyst at a temperature of 170° C. and 180° C. respectively. It is indicated that the polymerisation of 5-membered glycerol cyclic carbonates to form poly(ethylene carbonate) or poly(propylene carbonate) compounds is thermodynamically unfavourable and that this polymerisation is accompanied by major decarboxylation and release of $CO_2$ correlated with the formation of poly (ether-carbonate(s)) having a proportion of carbonate function of no more than 50% in moles. Said polymerisation also requires starting products of petrochemical origin (ethylene carbonate and propylene carbonate), a very long reaction time—in particular of several days—and is incompatible with application on an industrial scale. In addition, the said method only leads to oligomers of low molecular weight.

It was therefore not possible up until now to obtain α/α'-alkoxylated glycerol linear carbonic esters, in particular in the form of oligomers, in less than 24 hours and under conditions compatible with application on an industrial scale.

The invention sets out to overcome these shortcomings.

SUMMARY

The invention is therefore directed to a method allowing novel compounds to be obtained, called α/α'-alkoxylated glycerol linear carbonic esters, comprising at least one repeat unit resulting from the opening of the 5-membered ring of a glycerol cyclic carbonate, wherein at least one of the α/α' carbons of the glycerol-derived group forms a covalent ether-oxide bond with an organic group which, in relation to the repeat unit derived from the glycerol carbonate, forms a side chain of <<alkoxy>> type (ether-oxide).

The invention also sets out in particular to propose a said method able to be implemented under conditions compatible with application on an industrial scale, in particular at moderate temperature and with short reaction times—in particular less than 24 hours—in simple low-cost manner using reagents derived from natural resources—plant resources in particular—and that are renewable.

The invention also sets out in particular to propose a method with which it is possible to obtain an organic composition of α/α'-alkoxylated glycerol linear carbonic esters that is directly usable.

The invention also sets out to propose a said method with which it is possible to insert heteroatomic functional groups—in particular amino or oxygenated groups—in α/α'-alkoxylated glycerol linear carbonic esters, in particular in the form of oligomers, at the time of synthesis thereof.

The invention also sets out to propose a said method allowing the synthesis of novel alkoxylated glycerol linear carbonic esters, in particular in the form of oligomers—of controlled molecular weight which can be varied. In particular, the invention also sets out to propose a said method which allows the synthesis of novel alkoxylated glycerol linear carbonic esters—in particular in oligomer form—having a molecular weight higher than 500 g/mole and in particular higher than 1000 g/mole.

In particular, the invention sets out to propose a said synthesis method which allows the re-utilization of a plant resource such as glycerol which is an abundant, available co-product derived from the manufacture of biodiesel. The invention also sets out to propose a said method which does not require the use of a cyclic carbonate of petrochemical origin (such as glycerol ethyloxy-cyclocarbonate or glycerol propyloxy-cyclocarbonate). The invention also sets out to propose a said synthesis method which does not require the use of a hydrocarbon solvent derived from a fossil source that is toxic for the environment and human health and is non-renewable.

The invention also sets out in particular to propose novel alkoxylated glycerol linear carbonic esters, in particular in the form of oligomers, first having chemical resistance—in particular resistance to hydrolysis—which is improved and secondly that are biodegradable in particular via enzymatic route.

The invention also sets out in particular to propose novel alkoxylated glycerol linear carbonic esters—in particular in oligomer form—allowing modulation of the rheological properties of a composition containing the same.

In particular, the invention also sets out to propose novel alkoxylated glycerol linear carbonic esters particularly in the form of oligomers—having a least one organic side chain of polarity substantially close to the polarity of the C—C bond between two sp3 carbon atoms.

The invention sets out in particular to propose novel alkoxylated glycerol linear carbonic esters—in particular in the form of oligomers—of low polarity yet having main chain terminal ends that are adapted to increase the affinity thereof for a surface—in particular for a metal surface.

The invention also sets in particular to propose novel alkoxylated linear glycerol carbon esters—in particular in the form of oligomers—able to be obtained from natural renewable resources and which can be qualified as being <<bio-based>>.

DETAILED DESCRIPTION

Throughout the text by:
- <<α carbon>> and/or <<α' carbon>> of a glycerol derivative is meant the two carbon atoms carrying two hydrogen atoms, and by <<β carbon>> of a glycerol derivative is meant the carbon atom carrying a single hydrogen atom;
- <<glycerol linear carbonic ester>> is meant any compound able to be obtained by opening the carbonate ring of a glycerol cyclic carbonate;
- <<main chain>> of an alkoxylated glycerol linear carbonic ester is meant the set of atoms of highest cardinality of the alkoxylated glycerol linear carbonic ester which are linearly bonded to one another and comprising at least one of the α and/or α' carbon atoms of glycerol and the β carbon atoms of glycerol;
- <<side chain>> of an alkoxylated glycerol linear carbonic ester is meant the set of atoms linearly bonded to one another by the covalent bonds, the said set of atoms being separate from the main chain and attached to the said main chain by an ether-oxide group —$CH_2$—O—.
- <<bio-based>> means able to be obtained from natural renewable resources.

The invention therefore concerns a method for synthesizing novel α/α'-alkoxylated glycerol linear carbonic esters—in particular in the form of oligomers—wherein the following are contacted:
  i. a quantity of at least one precursor selected from the group formed by α/α'-alkoxylated glycerol cyclic carbonates of following formula (XXII):

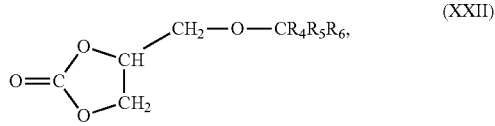

wherein $R_4$, $R_5$ and $R_6$ are selected from the group formed by hydrogen (H) and organic groups formed of at least two atoms attached by covalent bonds, the said atoms belonging to the group formed by carbon (C), hydrogen (H), oxygen (O) and nitrogen (N); and
  ii. a quantity of at least one catalyst selected from the group formed by metal oxides, metal alkoxides, Lewis acids, organometallic catalysts and mineral bases;
  iii. a quantity of at least one organic initiator selected from the group formed by alcohols, polyols and aminoalcohols;

at a reaction temperature lower than 220° C., in particular between 100° C. and 220° C. and more particularly between 150° C. and 220° C.—further particularly between 140° C. and 200° C., preferably substantially in the order of 180° C., characterized in that at a first step the precursor(s), the catalysts(s) and the organic initiator(s) are mixed and heated in a gas-tight sealed reactor to reach the reaction temperature and a pressure called autogenous pressure higher than atmospheric pressure within the sealed reactor, then at the reaction temperature and at a second step escape of gaseous composition is allowed to reduce the pressure in the reactor and the reaction temperature is maintained in the reactor for a time of more than 5 minutes.

The invention therefore concerns a method for synthesizing novel α/α'-alkoxylated glycerol linear carbonic esters—in particular in the form of an oligomer of an α/α'-alkoxylated glycerol linear carbonic ester—by catalytic opening of the five-membered ring of an α/α'-alkoxylated glycerol cyclic carbonate precursor and oligomerization in the presence of a catalyst—e.g. a Lewis or transesterification catalyst—and of an organic initiator which may be monofunctional or polyfunctional.

In fully unexpected manner, the treatment of a precursor selected from the group formed by α/α' alkoxylated glycerol cyclic carbonates of formula (XXII) in the presence both of a catalyst and of an organic initiator proves to be sufficient to allow opening of the five-membered cyclic carbonate ring at a reaction temperature lower than 220° C. and to obtain α/α'-alkoxylated glycerol linear carbonic esters—in particular in oligomer form—without total loss of the carbonate groups. One possible explanation for this surprising phenomenon is that the catalyst allows the catalytic opening of the ring of a first precursor by the organic initiator and in synergy the attack of the initiation product thus formed on a second precursor leading to oligomerization:
  either via preferred nucleophilic attack by a hydroxyl of the organic initiator on the carbonyl carbon of the α/α' alkoxylated glycerol cyclic carbonate precursor of formula (XXII), leading to the formation of an α/α'-alkoxylated glycerol linear carbonic ester;
  or via minority nucleophilic attack by a hydroxyl of the organic initiator on one of the carbon atoms of the ring of the α/α'-alkoxylated glycerol cyclic carbonate precursor of formula (XXII), leading to the irreversible formation of an ether group via spontaneous decarbonatation and release of a hydroxyl group.

The inventors have discovered that it is possible to conduct the synthesis of a said α/α'-alkoxylated glycerol linear carbonic ester within a short time—in particular in the order of 2 hours—by contacting in a reactor an α/α'-alkoxylated glycerol cyclic carbonate precursor of formula (XXII), a catalyst and an organic initiator at a reaction temperature lower than 220° C. and under pressure called autogenous pressure generated by heating the reaction mixture in a hermetically-sealed reactor.

Advantageously, when the mixture reaches the reaction temperature, the reactor is opened and the inner pressure of the reactor is equilibrated with atmospheric pressure.

The inventors have observed that the placing under overpressure of the reactor containing the mixture formed of each precursor, of each catalyst and of each organic initiator does not cause the decomposition of the precursor into α,α'-alkoxylated glycerol and carbon dioxide, but on the contrary allows opening of the precursor cyclic carbonate ring and oligomerization of the precursor induced by the organic initiator and the formation of a novel α/α'-alkoxylated glycerol linear carbonic ester.

In one method of the invention the formed composition is heated in the hermetically sealed reactor up to a reaction temperature lower than 220° C. The heating of the composition in the hermetically sealed reactor generates pressure called autogenous pressure. When the reaction temperature is reached, escape of gaseous composition from the reactor is allowed to reduce the pressure in the reactor. This promotes the formation of novel α/α'-alkoxylated glycerol linear carbonic esters—in particular in oligomer form—meeting formula (VI) given below and wherein x equals 1.

Advantageously and according to the invention, when the formed mixture reaches the reaction temperature the reactor is opened to reduce the inner pressure of the reactor. To do so:
  gaseous composition is allowed to escape from the reactor so as to adjust the pressure of the said reactor at a value between the value of atmospheric pressure and the value of so-called autogenous pressure reached inside the sealed reactor at the reaction temperature; and
  the reaction temperature is maintained for an adapted time to allow polymerisation of at least part of the amount of α/α'-alkoxylated glycerol cyclic carbonate precursor of formula (XXII) and the formation of novel α/α'-alkoxylated glycerol linear carbonic esters—in particular in oligomer form.

When the reaction mixture has reached the reaction temperature, a decompression valve of the reactor is opened to place the reaction mixture substantially at atmospheric pressure and the reaction mixture is held at reaction temperature.

Advantageously and according to the invention, the heating of the composition in the reactor is continued for a reaction time of between 1 hour and 24 hours at atmospheric pressure, in particular for between 1 hour and 6 hours, preferably in the order of 2 hours.

Advantageously the synthesis is conducted in a gas-tight reactor so as to control decarboxylation and $CO_2$ retention in the oligomer by controlling the ceiling reaction temperature (e.g. 170° C.) and ceiling pressure (in the order of 3 bars). In the main chain the oligomer alternates linear propylene carbonate groups and propylene groups carrying O-alkoxylated methyl repeat units forming side chains. The retaining of $CO_2$ in the oligomer is in the order of 30-50 mol/%.

In fully surprising manner the treatment of a precursor selected from the group formed by α/α'-alkoxylated glycerol cyclic carbonates of formula (XXII) in the presence both of a catalyst and of an organic initiator, wherein the autogenous pressure is modulated inside the reactor, proves to lead preferably selectively to a hetero-oligomer comprising α/α'-alkoxylated glycerol linear carbonic ester repeat units (x=1 in formula (VI) shown below and α/α'-alkoxylated glycerol repeat units (x=0 in formula (VI) shown below).

Advantageously, at the second step the reaction temperature is held for a time of between 5 minutes and 6 hours.

Advantageously, the organic initiator is a nucleophilic organic initiator adapted to allow nucleophilic attack of the precursor and the formation of novel α/α'-alkoxylated glycerol linear carbonic esters—in particular in oligomer form—having one functionalised terminal end—in particular an amino terminus.

Advantageously and according to the invention, at least one organic initiator is a polyol. Advantageously and according to the invention, at least one organic initiator is glycerol. Advantageously the choice of glycerol as organic initiator allows the obtaining of an α/α'-alkoxylated glycerol linear carbonic ester which is <<bio-based>>.

Advantageously and according to the invention, the organic initiator is selected from the group formed by aliphatic organic groups i.e. not having any aromatic group (hydrocarbon or heterocyclic).

Advantageously and according to the invention, at least one organic initiator is selected from the group formed by amino-alcohols having at least one amine selected from the group formed by primary amines, secondary amines and tertiary amines.

Advantageously and according to the invention, at least one organic initiator is triethanolamine. Triethanolamine is therefore selected as the organic initiator comprising a tertiary amine.

Advantageously and according to the invention, at least one organic initiator is selected from the group formed by amino-alcohols having a main chain comprising 2 to 10 carbon atoms—in particular $NH_2$—$(CH_2)_z$—OH wherein z is an integer between 2 and 10 e.g. ethanolamine ($NH_2$—$CH_2$—$CH_2$—OH)—.

Advantageously and according to the invention, at least one organic initiator is selected form the group formed by 1-amino-1-cyclopentanemethanol, 4-aminocyclohexanol, amino-1-butanol, 2-amino-1-butanol, 2-amino-1-phenyl-1,3-propanediol, 3-amino-3-phenylpropan-1-ol and 2-amino-3-phenyl-1-propan-1-ol.

Advantageously the organic initiator is adapted so that it can react with the precursor in the liquid reaction medium at the reaction temperature. Advantageously in particular and according to the invention, the organic initiator has a sufficiently high boiling point adapted to allow an initiation reaction with the precursor at the reaction temperature.

The choice of α/α'-alkoxylated precursor and of organic initiator placed in the presence of the catalyst under autogenous pressure allows the obtaining of an α/α'-alkoxylated glycerol linear carbonic ester, in particular an oligomer of an α/α'-alkoxylated glycerol linear carbonic ester having a mole proportion of glycerol carbonic ester group relative to the total monomer number of between 30% and 50%.

The combination of the ceiling reaction temperature of below 220° C. and a pressure equal to or higher than atmospheric pressure, in particular a pressure of between 1000 and 5000 hPa, more particularly in the order of 3000 hPA provides the conditions for ring opening of the α/α'-alkoxylated glycerol cyclic carbonate precursor and for at least partial retaining of the carbonate group in the oligomer of α/α'-alkoxylated glycerol linear carbonic ester. The precursor/organic initiator tandem promotes the contacting of the precursor with the organic initiator. The catalyst completes the whole reaction system.

Advantageously and according to the invention, a catalyst is selected from the group formed by metal salts—in particular Lewis acids of metal sulfate type, particularly zinc sulfate ($ZnSO_4$)—sulfates on a cationic resin substrate and organometallic salts e.g. zinc carboxylates—in particular zinc stearate ($CH_3$—$(CH_2)_{16}$—$COO_2Zn$), tin carboxylates—in particular tin stearate, and zirconium carboxylates—in particular zirconium stearate. A said metal salt as catalyst is able to form a complex between the metal of the catalyst and the oxygen atom of the precursor carbonyl.

Advantageously and according to the invention, at least one catalyst is selected from the group formed by zinc sulfate and zinc stearate.

As a variant, advantageously and according to the invention, a catalyst is selected from the group form by metal oxides—e.g. zirconium oxide ($ZrO_2$) and titanium oxide ($TiO_2$).

As a variant and advantageously according to the invention, a catalyst is selected from the group formed by metal alkoxides. Advantageously a catalyst is selected from the group formed by $Ti(OR)_4$ and $Zr(OR)_4$ wherein R is an alkyl.

As a variant and advantageously according to the invention, a catalyst is selected from the group formed by metal acetylacetonates e.g. aluminium acetylacetonate.

As a variant and advantageously according to the invention, a catalyst is selected from the group formed by metal alkyls e.g. $(CH_3-CH_2)_2Zn$ as organometallic catalyst.

As a variant and advantageously according to the invention, a catalyst is selected from the group formed by mineral bases e.g. potassium carbonate ($K_2CO_3$), sodium carbonate ($Na_2CO_3$) and potassium hydroxide (KOH), sodium hydroxide (NaOH), barium hydroxide (BaOH). A said mineral base used as catalyst in a method according to the invention allows the formation of a nucleophilic organic initiator—in particular an alcoholate—able to react with the precursor cyclic carbonate and to form an ether bond via decarboxylation. In particular, a said catalyst is selected from the group formed by mineral bases capable of increasing the nucleophilicity of the organic initiator, in particular to form a hetero-oligomer of an α/α'-alkoxylated glycerol linear carbonic ester comprising at least one non-carbonatated glycerol repeat unit.

Advantageously, the catalyst is selected from the group formed by homogeneous catalysts. Advantageously it is also possible to choose the catalyst from the group formed by heterogeneous catalysts.

As a variant and advantageously according to the invention, an organometallic catalyst is selected.

Depending on the constituent heteroatoms of the organic initiator, heteroatom elements are inserted in the oligomer—in particular nitrogen and oxygen.

Advantageously and according to the invention, the molar ratio of the initial amount of precursor and the initial amount of organic initiator in the reactor is between 3 and 10, in particular between 4 and 6. A said molar ratio is adapted to allow a precursor conversion yield of between substantially 20% and substantially 80%.

The invention also extends to the novel α/α'-alkoxylated glycerol linear carbonic esters in the form of oligomers able to be obtained using a method of the invention.

The invention therefore also extends to the novel compounds of α/α'-alkoxylated glycerol linear carbonic esters of following general formula (VI):

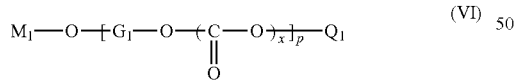
(VI)

where:
p is an integer higher than 1 and differing from 1; and
x is an integer equal to 0 or 1 possibly varying in formula (VI) in each group of formula (VI-a):

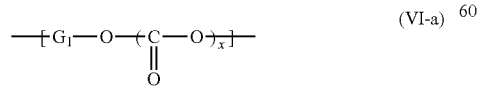
(VI-a)

x not always being zero; and
$M_1$ is selected from the group form by hydrogen (H) and organic groups formed of at least two atoms attached by covalent bonds, the said atoms belonging to the group formed by carbon (C), hydrogen (H), oxygen (O) and nitrogen (N); and $Q_1$ is an organic group formed of at least two atoms attached by covalent bonds, the said atoms belonging to the group formed by carbon (C), hydrogen (H), oxygen (O) and nitrogen (N); and G1 is an α/α'-alkoxylated propyl group of following general formula (II'):

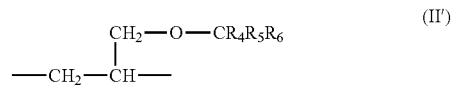
(II')

where $R_4$, $R_5$ and $R_6$ are selected from the group formed by hydrogen (H) and organic groups formed of at least two atoms attached via covalent bonds, the said atoms belonging to the group formed by carbon (C), hydrogen (H), oxygen (O) and nitrogen (N).

The invention therefore concerns α/α'-alkoxylated glycerol linear carbonic esters in the form of oligomers of general formula (VI) comprising at least one group of atoms selected from α/α'-alkoxylated propyl groups of formula (II') and wherein one of the carbons a or a' of glycerol in the α/α'-alkoxylated propyl group of formula (II) has an ether-oxide covalent bond with an organic group—in particular with a hydrocarbon group. The novel compounds of the invention are therefore α/α'-alkoxylated glycerol linear carbonic esters of formula (VI) in the form of oligomers. In these novel compounds, the alkoxy group is attached to the α/α'-alkoxylated propyl group of formula (II') by the oxygen atom of one of the primary hydroxyls of the α/α'-alkoxylated propyl group of formula (II') and forms a side chain of the said α/α'-alkoxylated glycerol linear carbonic ester of formula (VI).

Advantageously, the ether-oxide bond between the main chain and each side chain of an α/α'-alkoxylated glycerol linear carbonic ester of formula (VI) according to the invention has reduced polarity compared with an ester bond. For example the dipolar moment of the ethyl ether of glycerol carbonate is 4.36 Debye, whereas the dipolar moment of the acetate of glycerol carbonate is 6.19 Debye.

More particularly, the invention concerns the novel compounds of α/α'-alkoxylated glycerol carbonic esters in oligomer form according to following general formula (III):

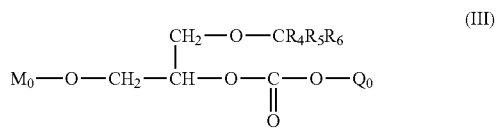
(III)

where:
$M_0$ is selected from the group formed by hydrogen (H) and organic groups formed of at least two atoms attached via covalent bonds, the said atoms belonging to the group formed by carbon (C), hydrogen (H), oxygen (O) and nitrogen (N); and $Q_0$ is an organic group formed of at least two atoms attached via covalent bonds, the said atoms belonging to the group formed by carbon (C), hydrogen (H), oxygen (O) and nitrogen (N).

The invention also concerns the novel α/α'-alkoxylated glycerol linear carbonic ester compounds of following general formula (IV):

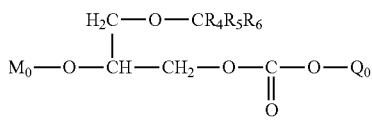

where:
$M_0$ is selected from the group formed by hydrogen (H) and organic groups formed of at least two atoms attached via covalent bonds, the said atoms belonging to the group formed by carbon (C), hydrogen (H), oxygen (O) and nitrogen (N); and
$Q_0$ is an organic group formed of at least two atoms attached via covalent bonds, the said atoms belonging to the group formed by carbon (C), hydrogen (H), oxygen (O) and nitrogen (N).

The α/α'-alkoxylated glycerol linear carbonic esters of formula (VI), of formula (III) or of formula (IV) according to the invention are synthetic oligomers obtained from a natural renewable resource. Such oligomers have at least two α/α'-alkoxylated groups of following formula (II):

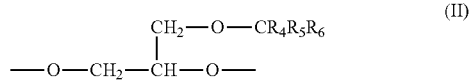

the two α/α'-alkoxylated groups of formula (II) being attached to one another via an ether bond (—O—) or via a carbonic di-ester bond (—O—CO—O—).

These oligomers are formed of a main chain which comprises a sequence of carbonatated α/α'-alkoxylated propyl groups. They have viscosity, thixotropy and polarity properties which may vary and can be adjusted according to needs and applications.

The invention extends in particular to oligomers of formula (VI) comprising between p=2 and p=50 α/α'-alkoxylated propyl groups $G_1$ of formula (II'). The α/α'-alkoxylated glycerol linear carbonic esters of the invention may also be polymers comprising more than 50—advantageously between 50 and 500, preferably between 50 and 100-α/α'-alkoxylated propyl groups $G_1$ of formula (II').

The invention advantageously and more particularly concerns oligomers of α/α'-alkoxylated glycerol linear carbonic esters having between 2 and 10 α/α'-alkoxylated propyl groups $G_1$ of formula (II').

Advantageously and according to the invention, $Q_0$ represents the —CH$_2$—CH$_2$—NH$_2$ group in the α/α'-alkoxylated glycerol linear carbonic esters of formula (III) or formula (IV). Advantageously and according to the invention, $Q_1$ represents the —CH$_2$—CH$_2$—NH$_2$ group in the α/α'-alkoxylated glycerol linear carbonic esters of formula (V) or formula (VI). Advantageously, $Q_3$ represents the —CH$_2$—CH$_2$—NH$_2$ group in the α/α'-alkoxylated glycerol linear carbonic esters of formula (VIII) or formula (IX).

Advantageously and according to the invention, the groups $R_4$, $R_5$ and $R_6$ are hydrogens (H). Each group $G_1$ of the compounds of formula (VI) is then an α/α'-methoxylated propyl group.

According to some particular and advantageous embodiments of compounds according to the invention, $R_4$ and $R_5$ are hydrogens (H) and $R_6$ is an alkyl group having 1 to 5 carbon atoms.

According to other particular and advantageous embodiments of compounds of the invention, the groups $R_4$ and $R_5$ are hydrogens (H) and group $R_6$ is a methyl. Each group $G_1$ of the compounds of formula (VI) is then an α/α'-ethoxylated propyl group.

According to other particular advantageous embodiments of the invention, the groups $R_4$ and $R_5$ are hydrogen (H) and group $R_6$ is an ethyl. Each group $G_1$ of the compounds of formula (VI) is then an α/α'-propoxylated propyl group.

According to other particular advantageous embodiments of the compounds of the invention, $R_4$ and $R_5$ are hydrogens (H) and $R_6$ is an amino hydrocarbon group in particular an aliphatic amino hydrocarbon group or aromatic amino hydrocarbon group. In particular $R_4$ and $R_5$ are hydrogens (H) and $R_6$ is an amino-alkyl group having 1 to 5 carbon atoms.

According to other particular advantageous embodiment of compounds of the invention, the groups $R_4$ and $R_5$ are hydrogens (H) and group $R_6$ is a methylamine group of formula: —CH$_2$—NH$_2$.

Advantageously and according to the invention, $R_4$, $R_5$ and $R_6$ are selected from the group formed by hydrogen (H) and organic groups of following general formula (VII):

where:
$R_7$ is selected from the group formed of an H and a hydrocarbon group having 1 to 6 carbon atoms;
m is an integer between 0 and 10 inclusive; and
X is selected from among —O— and —NH—.

The α/α'-alkoxylated glycerol linear carbonic esters of the invention conforming to formula (VI) may have at least one side chain having at least one atom or group of atoms selected from among an oxygen atom (—O—), a secondary amine (—NH—) and a tertiary amine.

The invention more particularly concerns α/α'-alkoxylated glycerol linear carbonic esters in the form of oligomers according to following general formula (VIII):

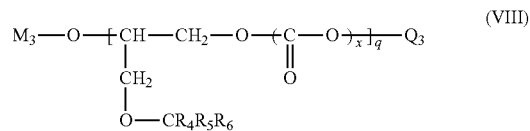

where:
q is an integer higher than 1 and differing from 1; and
x is an integer equal to 0 or 1 possibly varying in formula (VIII) in each group (VIII-a):

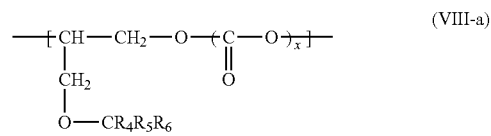

x not always being zero; and
$M_3$ is selected from the group formed by hydrogen (H) and organic groups formed of at least two atoms attached via covalent bonds, the said atoms belonging to the group formed by carbon (C), hydrogen (H), oxygen (O) and nitrogen (N); and $Q_3$ is an organic group formed of at least two atoms attached via covalent bonds, the said atoms belonging to the group formed by carbon (C), hydrogen (H), oxygen (O) and nitrogen (N).

The invention more particularly concerns α/α'-alkoxylated glycerol linear carbonic esters in the form of oligomers according to following general formula (IX):

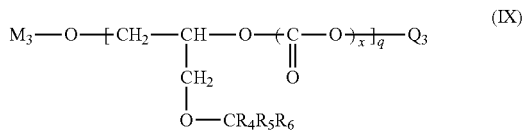

where:

q is an integer higher than 1 and differing from 1; and x is an integer equal to 0 or 1 possibly varying in formula (IX) in each group of formula (IX-a):

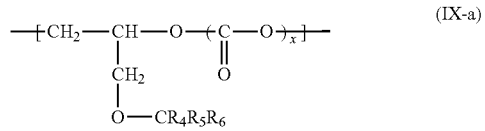

x not always being zero; and $M_3$ is selected from the group formed by hydrogen (H) and organic groups formed of at least two atoms attached via covalent bonds, the said atoms belonging to the group formed by carbon (C), hydrogen (H), oxygen (O) and nitrogen (N); and $Q_3$ is an organic group formed of at least two atoms attached via covalent bonds, the said atoms belonging to the group formed by carbon (C), hydrogen (H, oxygen (O) and nitrogen (N).

An α/α'-alkoxylated glycerol linear carbonic ester oligomer of the invention comprises at least one first α/α'-alkoxylated group of formula (II) where:

the oxygen atom of one of the carbons (α, α') of the first α/α'-alkoxylated glycerol group of formula (II) is engaged in an ether-oxide bond with an organic group of general formula —$CR_4R_5R_6$ and;

the oxygen atom of the other carbon (α, α') of the first α/α'-alkoxylated group of formula (II) and the oxygen atom of carbon (β) of the first α/α'-alkoxylated group of formula (II) are engaged one in a bond with a di-ester carbonic group (—O—CO—O—) or in an ether bond (—O—) with a second α/α'-alkoxylated group of formula (II), and the other in an ether bond with a group of atoms of formula $M_0$-O— or $M_1$-O— or $M_3$-O—.

Advantageously the α/α'-alkoxylated glycerol linear carbonic esters of the invention under infrared spectrometry analysis exhibit a vibration band of between 1730 cm$^{-1}$ and 1750 cm$^{-1}$.

According to a first variant of the invention, some α/α'-alkoxylated glycerol linear carbonic esters are homo-oligomers of α/α'-alkoxylated glycerol carbonic esters of following general formula (V):

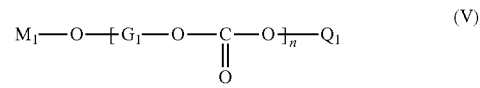

where n is an integer higher than 1 and differing from 1.

A said homo-oligomer of α/α'-alkoxylated glycerol carbonic ester of formula (V) has a repeat of one same group of following formula (V-a):

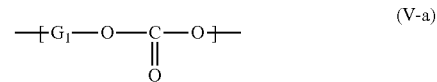

this group of formula (V-a) being present at least twice in the main chain.

In particular, the invention concerns homo-oligomers of α/α'-alkoxylated glycerol linear carbonic esters of formula (VI) wherein x is constant and always equals 1 in all the groups of formula (VI-a).

The oligomers of α/α'-alkoxylated glycerol linear carbonic esters of the invention may be hetero-oligomers i.e. they may have at least one α/α'-alkoxylated propyl carbonate group (x=1) and at least one group selected from among the groups formed by α/α'-alkoxylated propyl groups (x=0). These hetero-oligomers of alkoxylated glycerol linear carbonic esters may also be formed of at least one α/α'-alkoxylated propyl carbonate group (x=1) and at least one α/α'-alkoxylated propyl group (x=0) linked to one another.

The hetero-oligomers of α/α'-alkoxylated glycerol linear carbonic esters of the invention may have regular or irregular alternation of alkoxylated glycerol linear carbonic ester repeat units (x=1) and alkoxylated glycerol repeat units (x=0).

Advantageously and according to the invention $M_0$, $M_1$ and $M_3$ are hydrogens (H). The main chain of a compound of the invention then comprises a single hydroxyl at one of the ends of the said main chain.

Advantageously, a compound of the invention, on at least part of the length of its main chain and forming the latter, comprises a homo-oligomer of an α/α'-alkoxylated glycerol linear carbonic ester.

In an oligomer of the invention, at least two of three carbon atoms of the α/α'-alkoxylated group of formula (II) form—in particular in combination with the linear carbonic ester groups—the main chain of the oligomer.

The invention more particularly concerns the α/α'-alkoxylated glycerol carbonic esters in the form of oligomers according to formula (VI) and comprising at least one amine group selected from the group formed of primary amines, secondary amines and tertiary amines. Said amino α/α'-alkoxylated glycerol carbonic esters of formula (VI) have improved adhesion properties with a metal surface and on a cellulose surface.

Advantageously and according to the invention, $Q_0$, $M_0$, $Q_1$, $M_1$, $Q_3$ and $M_3$ are selected independently of each other from the group formed by organic groups formed of at least two atoms attached via covalent bonds, the said atoms belonging to the group formed by carbon (C), hydrogen (H), oxygen (O) and nitrogen (N) and having no more than 10—in particular 5—carbon atoms.

Advantageously and according to the invention, $Q_0$, $Q_1$ and $Q_3$ are selected from the group formed by aliphatic groups—in particular hydrocarbon aliphatic groups.

Advantageously and according to the invention, $Q_0$, $Q_1$ and $Q_3$ are selected from the group formed by amino hydrocarbon groups. Advantageously and according to the invention $Q_0$, $Q_1$ and $Q3$ are —$CH_2$—$CH_2$—$NH_2$.

Advantageously and according to the invention $Q_0$, $Q_1$ and $Q_3$ are selected from the group formed by oxygenated amino hydrocarbon groups.

Advantageously an α/α'-alkoxylated glycerol linear carbonic ester of formula (VI) according to the invention has a molar mass higher than 200 g/mole, in particular higher than 600 g/mole, in particular higher than 1000 g/mole, preferably between 1000 g/mole and 3000 g/mole, more preferably in the order of 2500 g/mole.

Advantageously an α/α'-alkoxylated glycerol linear carbonic ester of formula (VI) according to the invention has a hydroxyl number expressed in milligrams of KOH per gram of compound calculated according to standard NF T600-213 of between 200 and 2000 mg KOH/g of compound.

The invention also concerns a composition—in particular a liquid composition—comprising at least one α/α'-alkoxylated glycerol linear carbonic ester oligomer according to the invention.

Advantageously and according to the invention, the composition comprises in a mixture a plurality of α/α'-alkoxylated glycerol linear carbonic ester oligomers, each α/α'-alkoxylated glycerol linear carbonic ester oligomer of the organic composition meeting at least one of the general formulas (III), (IV), (V), (VI), (VIII) and (IX).

A composition of the invention is an organic composition which advantageously further comprises at least one compound selected from the group formed by α/α'-alkoxylated glycerol cyclic carbonates of formula (XXII).

The invention also concerns a method for synthesizing α/α'-alkoxylated glycerol linear carbonic esters—in particular in oligomer form, α/α'-alkoxylated glycerol linear carbonic esters in the form of oligomers, a composition incorporating at least one said α/α'-alkoxylated glycerol linear carbonic ester in oligomer form, and the uses thereof, characterized by a combination of all or part of the characteristics indicated above or below.

Other objectives, characteristics and advantages of the invention will become apparent on reading the following description comprising examples given solely as non-limiting illustrations.

To implement a method for synthesizing novel α/α'-alkoxylated glycerol linear carbonic esters a quantity of at least one precursor of formula (XXII), a quantity of at least one catalyst and a quantity of at least one organic initiator are placed in contact. It is possible to obtain the α/α'-alkoxylated linear glycerol cyclic carbonate precursor of formula (XXII) using a method derived from the method described in FR 2 778 182.

Therefore to implement a synthesis method according to the invention, first O-etherification of glycerol carbonate is performed so as to form the α/α'-alkoxylated glycerol cyclic carbonate precursor of formula (XXII), after which the precursor is subjected to a synthesis method of the invention to form an α/α'-alkoxylated glycerol linear carbonic ester oligomer of general formula (VI) wherein the alkoxyl group is attached to the oligomer via a spacer methylene group of the main chain of the oligomer.

It is also possible to obtain the α/α'-alkoxylated glycerol cyclic carbonate precursor of formula (XXII) via other synthesis routes, in particular by reacting:

a glycerol ether of formula (XXVI):

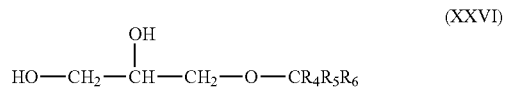

with:
a carbonate selected from the group formed of dialkyl carbonates—in particular dimethyl carbonate and diethyl carbonate—and alkylene carbonates and in particular ethylene carbonate and propylene carbonate,
in the presence of potassium carbonate ($K_2CO_3$) at a temperature in the order of 75° C. Variants of said synthesis route are described in Examples 1 and 2.

It is also possible to obtain the alkoxylated glycerol cyclic carbonate precursor of formula (XXII) by reacting:
glycerol with:
a carbonate selected from the group formed by dialkyl carbonates—in particular dimethyl carbonate and diethyl carbonate—and alkylene carbonates in particular ethylene carbonate and propylene carbonate,
at a temperature higher than 200° C.—in particular in the order of 230° C.—in the presence of alumina ($Al_2O_3$). A variant of said synthesis route is described in Example 3.

It is also possible to prepare α/α'-alkoxylated glycerol cyclic carbonate of formula (XXII) by reacting:
glycerol cyclic carbonate with:
a carbonate selected from the group formed by dialkyl carbonates—in particular dimethyl carbonate and diethyl carbonate—and alkylene carbonates in particular ethylene carbonate and propylene carbonate,
at a temperature in the order of 200° C. in the presence of alumina ($Al_2O_3$). A variant of said synthesis route is described in Example 4.

It is also possible to prepare α/α'-alkoxylated glycerol cyclic carbonate of formula (XXII) by catalytic trans-carbonatation reaction of glycerol using an organic cyclic carbonate.

It is also possible to prepare α/α'-alkoxylated glycerol cyclic carbonate of formula (XXII) by reaction of an alcohol—in particular methanol, ethanol, iso-propanol or tert-butanol—on glycerol in the presence of a cationic resin (e.g. an Amberlyst® resin, zeolite, sulfonic acid grafted on silica, mesoporous silica) as catalyst and at a temperature of between 60° C. and 200° C.

EXAMPLES

Example 1

Carbonatation of Glycerol α-Methyl-Ether

A 100 ml glass round-bottomed flask is charged with 1 molar equivalent of glycerol α-methyl-ether (3-methoxy-1,2-propanediol), CAS 623-39-2) and 3 molar equivalents of dimethyl carbonate (CAS 616-38-6) under mechanical stirring at a speed of 400 rpm and temperature of 75° C. in the presence of 0.03 molar equivalents of potassium carbonate (CAS 584-08-7) as catalyst for 8 hours. The methyl ether of glycerol cyclic carbonate (GCME) is formed with a yield after isolation of 85% compared with the starting glycerol α-methyl-ether.

Example 2

Carbonatation of Glycerol α-Ethyl-Ether

A 100 mL glass round-bottomed flask is charged with 1 molar equivalent of glycerol α-ethyl-ether (3-ethoxy-1,2-propanediol, CAS 1874-62-0) and 3 molar equivalents of dimethyl carbonate (CAS 616-38-6) under mechanical stirring at a speed of 400 rpm and temperature of 75° C. in the presence of 0.03 molar equivalents of potassium carbonate (CAS 584-08-7) as catalyst for 8 hours. The ethyl ether of glycerol cyclic carbonate is formed with a yield of 85% after isolation.

Example 3

Glycerol α-Methylation and Carbonatation

The methyl ether of glycerol cyclic carbonate (GCME) is prepared from glycerol. 1 molar equivalent of glycerol (CAS 56-81-5) and 10 molar equivalents of dimethyl carbonate (CAS 616-38-6) are placed in an autoclave at a temperature of 230° C. for 3 hours in the presence of 2 molar equivalents of neutral alumina ($Al_2O_3$) under mechanical stirring at 400 rpm. The glycerol cyclic carbonate methyl ether (GCME) is obtained with a yield of 50% determined by gas phase chromatography coupled to a flame ionization detector (GC-FID). The GCME is isolated by distillation under reduced pressure (18 hPa) at a temperature of 115° C.

Example 4

α-Methylation of Glycerol Cyclic Carbonate

Glycerol cyclic carbonate methyl ether (GCME) is prepared from glycerol cyclic carbonate. 1 molar equivalent of glycerol cyclic carbonate (CAS 931-40-8,4-hydroxymethyl-1,3-dioxolan-2-one or 4-hydroxymethyl-2-oxo-1,3-dioxolane) and 5 molar equivalents of dimethyl carbonate (CAS 616-38-6) are placed in an autoclave at a temperature of 200° C. for 4 hours in the presence of 1 molar equivalent of neutral alumina ($Al_2O_3$) and under mechanical stirring at 400 rpm. The glycerol cyclic carbonate methyl ether (GCME) is obtained with a yield of 66% determined by analysis of the reaction medium by gas phase chromatography coupled to a flame ionization detector (GC-DIF). The GCME is isolated by distillation under reduced pressure (18 hPa) at a temperature of 115° C.

By way of indication, it is also possible to prepare the glycerol cyclic carbonate according to the method described in document FR 2 733 232 by catalytic trans-carbonatation of glycerol from an organic cyclic carbonate.

Example 5

Oligomerization of the Glycerol Cyclic Carbonate Methyl Ether (GCME) in the Presence of Glycerol as Organic Initiator of Oligomerization A quantity of GCME, a quantity of glycerol as oligomerization initiator and a quantity of zinc sulfate as catalyst are placed in a 250 mL autoclave. Before the reaction the weight proportion of GCME and glycerol is 85:15 and the weight proportion of catalyst is 0.5% relative to the total weight of the reagents. After gas-tight hermetic sealing of the autoclave it is heated to bring the reaction medium to 180° C. At this temperature of 180° C. the reaction medium is placed at atmospheric pressure and this reaction temperature is held for a time of 2 hours under mechanical stirring at 400 rpm.

Under Fourier Transform Infrared spectroscopy (FTIR) of the reaction medium a strong reduction is observed in the intensity of the vibration band corresponding to the vibration frequency of the GCME carbonyl at 1790 $cm^{-1}$, and the onset of a band corresponding to the vibration frequency of the carbonyl of the linear carbonate at 1750-1730 $cm^{-1}$.

Example 6

Oligomerization of the Glycerol Cyclic Carbonate Methyl Ether (GCME) in the Presence of Glycerol as Oligomerization Initiator A quantity of CGME, a quantity of glycerol as oligomerization initiator and a quantity of zinc stearate (CAS 557-05-1, zinc bis-octadecanoate) as catalyst are placed in a 250 mL autoclave. Before the reaction the weight proportion of GCME and glycerol is 85:15 and the weight proportion of catalyst is 0.5% relative to the total weight of the reagents. After gas-tight hermetic sealing of the autoclave it is heated to bring the temperature of the reaction medium to 180° C. At this temperature of 180° C. the reaction medium is placed under atmospheric pressure and this reaction temperature is held for a time of 2 hours under mechanical stirring at 400 rpm.

Under $^{1H}$NMR analysis at 4.3 ppm and 3.57 ppm the signals are observed corresponding to the glycerol protons at positions 1-3 and 1-4 relative to the carbon of the linear carbonate. Also between 3.2 ppm and 3.5 ppm the signals are observed corresponding to the glycerol protons at positions 1-2 and 1-3 relative to the glycerol ether-oxide group.

The conversion rate of GCME (disappearance of the cyclic carbonate group), the conversion rate of oligomerization initiator (glycerol) and the mean molar mass of the formed oligomer are given in Table 1 below.

TABLE 1

| Oligomerization initiator | GCME conversion rate, % | Initiator conversion rate, % | Mean molar mass of the oligomer, g/mole |
| --- | --- | --- | --- |
| Glycerol | 95.3 | 88.7 | 2410 |

Example 7

Oligomerization of Glycerol Cyclic Carbonate Methyl Ether (GCME) in the Presence of Ethanolamine as Oligomerization Initiator A quantity of GCME, a quantity of ethanolamine (CAS 141-43-5,2-amino-1-ethanol) as oligomerization initiator and a quantity of zinc stearate (CAS 557-05-1, zinc bis-octadecanoate) are placed in a 250 mL autoclave. Before the reaction the weight proportion of GCME and glycerol is 85:15 and the proportion of catalyst is 0.5% relative to the total weight of the reagents. After gas-tight hermetic sealing of the autoclave, it is heated to bring the temperature of the reaction medium to 180° C. At this temperature of 180° C. the reaction medium is placed under atmospheric pressure and this reaction temperature is held for a time of 2 hours under mechanical stirring at 400 rpm.

The conversion rate of GCME (disappearance of the cyclic carbonate group), the conversion rate of oligomerization initiator (2-amino-1-ethanol) and the mean molar mass of the α/α'-alkoxylated glycerol carbonic ester oligomers obtained are given in Table 2 below:

TABLE 2

| Oligomerization initiator | GCME conversion rate, % | Mean molar mass of the oligomer, g/mole |
|---|---|---|
| 2-amino-1-ethanol | 100 | 2460 |
| 2-amino-1-ethanol | 100 | 2440 |

It was found that 16% to 20% of the starting amino ethanolamine groups are contained in the oligomer obtained.

Analysis by Fourier transform infrared spectroscopy of the composition obtained by treating GCME with ethanolamine (EA) shows the complete disappearance of the signal at 1794 cm$^{-1}$ corresponding to the carbonyl of the GCME precursor and the onset of a signal at 1750 cm$^{-1}$ corresponding to the linear carbonic ester carbonyl of the oligomer obtained. This analysis did not show any signal at 1710 cm$^{-1}$ corresponding to the carbonyl of a linear urethane function.

Example 8

Oligomerization of a Mixture of GCME and Glycerol Cyclic Carbonate in the Presence of Ethanolamine as Oligomerization Initiator A quantity of GCME, a quantity of glycerol cyclic carbonate, a quantity of ethanolamine (CAS 141-43-5,2-amino-1-ethanol) as oligomerization initiator and a quantity of zinc stearate (CAS 557-05-1, zinc octadecanoate) are placed in a 250 mL autoclave. Before the reaction the weight proportion of GCME, of glycerol cyclic carbonate and of ethanolamine is 42.5:42.5:15 and the proportion of catalyst is 0.5% relative to the total weight of the reagents. After gas-tight hermetic sealing of the autoclave it is heated to bring the temperature of the reaction medium to 180° C. At this temperature of 180° C. the reaction medium is placed under atmospheric pressure and this reaction temperature is held for a time of 2 hours under mechanical stirring at 400 rpm.

Example 9

Oligomerization of the Glycerol Cyclic Carbonate Methyl Ether (GCME) in the Presence of 3-(2-hydroxyethyl)imidazolidin-2-one (HEI) as oligomerization initiator GCME, HEI as oligomerization initiator and zinc stearate (CAS 557-05-1, zinc octadecanoate) are placed in a 250 mL autoclave. Before the reaction, the weight proportion of CGME and of glycerol is 85:15 and the proportion of catalyst is 0.5 relative to the total weight of the reagents. After gas-tight hermetic sealing of the autoclave it is heated to bring the temperature of the reaction medium to 180° C. At this temperature of 180° C. the reaction medium is placed under atmospheric pressure and this reaction temperature is held for a time of 2 hours under mechanical stirring at 400 rpm.

The conversion rate of GCME (disappearance of the cyclic carbonate group), the conversion rate of the oligomerization initiator (HEI) and the mean molar mass of the oligomer obtained are given in Table 3 below.

TABLE 3

| Oligomerization initiator | GCME conversion rate, % | Initiator conversion rate, % | Mean molar mass of the oligomer, g/mole |
|---|---|---|---|
| HEI | 75.5 | 91.1 | 2460 |

Example 10

Oligomerization of Glycerol Cyclic Carbonate Methyl Ether (GCME) in the Presence of Glycerol A quantity of CGME, a quantity of glycerol and a quantity of catalyst are placed in a 250 mL autoclave at ambient temperature.

The autoclave is hermetically sealed and the composition is heated to bring its temperature to the reaction temperature. When this reaction temperature is reached, the reactor is placed under atmospheric pressure and the formed composition is held at this reaction temperature under mechanical stirring at 400 rpm.

The reaction temperature, type of catalyst, reaction time, weight ratio of precursor (GCME) and glycerol and the conversion rate of the precursor are given in Table 4 below.

TABLE 4

| Reaction temperature, ° C. | Catalyst | Reaction time, h | GCME/Glycerol, w/w | Conversion, % |
|---|---|---|---|---|
| 180 | Zn stearate | 2 | 20 | 10 |
| 180 | Zn stearate | 2 | 10 | 19 |
| 180 | Zn stearate | 3 | 5 | 72 |
| 180 | Zn stearate | 6 | 5 | 48.5 |
| 180 | Zn stearate | 3 | 4.5 | 77 |
| 180 | Zn stearate | 2 | 4.5 | 50 |
| 180 | Zn stearate | 2 | 4.5 | 64 |
| 180 | ZnSO$_4$ | 2 | 5.0 | 15.5 |
| 180 | K$_2$CO$_3$ | 2 | 5.9 | 100 |

Example 11

Oligomerization of Glycerol Cyclic Carbonate Methyl Ether (GCME) Catalysed by Zinc Stearate in the Presence of an Oligomerization Initiator At ambient temperature quantity of GCME, quantity of oligomerization initiator selected from among triethanolamine (TEA), ethanolamine (EA), ethane-1,2-diamine (EDA), pentacyclic glycerol carbonate (GC), glycerol α-methyl ether (GE), ethanol (EtOH) and n-butanol (BuOH) and quantity of zinc stearate are placed in a 250 mL autoclave.

The autoclave is hermetically sealed, and the composition formed is heated to bring its temperature to the reaction temperature. When this reaction temperature is reached the reactor is placed under atmospheric pressure and the formed composition is held at this reaction temperature under mechanical stirring at 400 rpm for 2 hours.

The reaction temperature, chemical type of oligomerization initiator, weight ratio of precursor (GCME) and initiator and precursor conversion rate are given in Table 5 below.

TABLE 5

| Temperature, °C. | Initiator | GCME/initiator, w/w | Conversion, % |
|---|---|---|---|
| 180 | TEA | 7.5 | 89.0 |
| 160 | EA | 3 | 84.4 |
| 180 | EA | 3 | 98.8 |
| 180 | EDA | 3.2 | 97.0 |
| 180 | GC | 5.5 | 19.8 |
| 180 | GE | 4.4 | 19.5 |
| 180 | EtOH | 2.2 | 11.4 |
| 180 | BuOH | 3.5 | 19.2 |

Analysis by Fourier transform infrared spectroscopy of the composition obtained by treating GCME with ethanolamine (EA) shows the complete disappearance of the signal at 1794 $cm^{-1}$ corresponding to the carbonyl of the GCME precursor and the onset of a signal at 1750 $cm^{-1}$ corresponding to the carbonyl of the linear carbonic ester of the oligomer obtained.

Analysis by Fourier transform infrared spectroscopy of the composition obtained by treating GCME with ethane-1,2-diamine (EDA) shows the complete disappearance of the signal at 1794 $cm^{-1}$ corresponding to the carbonyl of the GCME precursor and the onset of a majority signal at 1710 $cm^{-1}$ corresponding to the carbonyl of a urethane group and of a minority signal at 1750 $cm^{-1}$ corresponding to the carbonyl of the linear carbonate.

TABLE 6

| Initiator/Temperature °C. | Mn | Mw | Mz | Ip |
|---|---|---|---|---|
| EA/160 | 740 | 781 | 826 | 1.06 |
|  | 290 | 294 | 299 | 1.02 |
|  | 183 | 185 | 186 | 1.01 |
|  | 104 | 105 | 107 | 1.02 |
| EA/180 | 736 | 760 | 787 | 1.03 |
|  | 418 | 422 | 427 | 1.01 |
|  | 288 | 290 | 293 | 1.01 |
|  | 177 | 180 | 183 | 1.02 |
| TEA/180 | 421 | 428 | 438 | 1.02 |
|  | 292 | 295 | 298 | 1.01 |
|  | 170 | 173 | 175 | 1.01 |
| Glycerol/180 | 409 | 411 | 413 | 1.00 |
|  | 298 | 302 | 305 | 1.01 |
|  | 193 | 195 | 197 | 1.01 |
| Glycerol/$K_2CO_3$ | 637 | 705 | 821 | 1.11 |
|  | 395 | 398 | 401 | 1.01 |
|  | 291 | 294 | 296 | 1.01 |
| Glycerol/$ZnSO_4$ | 177 | 180 | 183 | 1.02 |

Analysis by gel permeation chromatography (GPC) of the compositions obtained in Examples 9 and 10 and described in Tables 4 and 5 is reported in Table 6 above wherein:

$M_n$ is the number average molecular weight of each oligomer of the composition expressed in g/mole;

$M_w$ is the weight average molecular weight of each oligomer of the composition expressed in g/mole;

$M_z$ is the centrifugation mean of each oligomer of the composition expressed in g/mole;

$I_p$ is the polydispersity index of each oligomer of the composition.

Example 12

Oligomerization of Glycerol Cyclic Carbonate Methyl Ether (GCME) Catalysed by Zinc Stearate in the Presence of an Organic Oligomerization Initiator About 30 g of GCME, ethanolamine (EA) as oligomerization initiator and a quantity of zinc stearate are placed in a 250 mL autoclave at ambient temperature.

The autoclave is hermetically sealed and the composition formed is heated to bring its temperature to the reaction temperature. When this reaction temperature is reached, the reactor is placed under atmospheric pressure and the composition obtained is held at this reaction temperature under mechanical stirring at 400 rpm.

The reaction temperature, molar ratio of GCME and ethanolamine and the number average molecular weight $M_n$ of each oligomer of the composition obtained (expressed in g/mole) are given in Table 7 below.

TABLE 7

| Temperature, °C. | GCMEA/EA, w/w | $Mn_1$ | $Mn_2$ | $Mn_3$ | $Mn_4$ |
|---|---|---|---|---|---|
| 180 | 10 | 691 | 411 | 290 | 179 |
| 200 | 3 | 682 | 412 | 288 | 180 |
| 180 | 3 | 736 | 418 | 288 | 177 |
| 160 | 3 | 740 | 290 | 183 | 104 |

This description is evidently given solely as an illustrative example and it is within the reach of persons skilled in the art to make numerous modifications, variants and applications thereto without departing from the scope of the invention, for example with respect to the choice of organic oligomerization initiator, the choice of alkoxylated glycerol cyclic carbonate precursor and choice of catalyst.

The invention claimed is:

1. A method for synthesizing a group of α/α'-alkoxylated glycerol linear carbonic esters wherein the following are placed in contact at a reaction temperature lower than about 220° C.:

i. a quantity of at least one precursor selected from the group consisting of α/α'-alkoxylated glycerol cyclic carbonates of a formula (XXII):

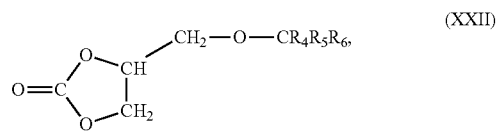

(XXII)

wherein $R_4$, $R_5$ and $R_6$ are hydrogen (H), or $R_4$ and $R_5$ are hydrogens (H) and $R_6$ is an alkyl group or an amino-alkyl group having 1 to 5 carbon atoms, or $R_4$, $R_5$ and $R_6$ are selected from the group formed by hydrogen (H) and organic groups of following general formula (VII):

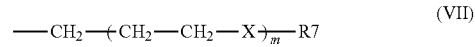

(VII)

wherein:

$R_7$ is selected from the group formed of an H and a hydrocarbon group having 1 to 6 carbon atoms;

m is an integer between 0 and 10 inclusive; and

X is selected from among —O— and —NH;

ii. a quantity of at least one catalyst selected from the group consisting of metal oxides, metal alkoxides, Lewis acids, organometallic catalysts and mineral bases; and iii. a quantity of at least one organic initiator selected from the group consisting of alcohols, polyols and amino-alcohols, wherein:

said alcohols are chosen from pentacyclic glycerol carbonate (GC), ethanol (EtOH), n-butanol (BuOH), and 3-(2-hydroxyethyl)imidazolidin-2-one, said polyols are chosen from glycerol and glycerol α-methyl ether (GE), and said amino-alcohols are chosen from amino-alcohols having a main chain comprising 2 to 10 carbon atoms;

wherein at a first step of the method the at least one precursor, the at least one catalyst and the at least one organic initiator are mixed and heated in a gas-tight sealed reactor until they reach the reaction temperature and a pressure called an autogenous pressure inside the sealed reactor which is higher than atmospheric pressure, and wherein at a second step of the method at the reaction temperature, a gaseous composition is allowed to escape to reduce the autogenous pressure inside the sealed reactor and the reaction temperature is maintained in the sealed reactor for a time of more than about 5 min.

2. The method according to claim 1, wherein the at least one organic initiator is selected from the group consisting of amino-alcohols having at least one amine selected from the group consisting of primary amines, secondary amines and tertiary amines.

3. The method according to one of claims 1, wherein the at least one organic initiator is triethanolamine.

4. The method according to claim 1, wherein the at least one organic initiator is selected from the group consisting of 1-amino-1-cyclopentanemethanol, 4-aminocyclohexanol, amino-1-butanol, 2-amino-1-butanol, 2-amino-1-phenyl-1,3-propanediol, 3-amino-3-phenyl propan-1-ol and 2-amino-3-phenyl-1-propan-1-ol.

5. The method according to claim 1, wherein the at least one catalyst is selected from the group consisting of zinc sulfate and zinc stearate.

\* \* \* \* \*